United States Patent
Viswanathan et al.

(10) Patent No.: US 10,588,700 B2
(45) Date of Patent: Mar. 17, 2020

(54) DISTORTION SUPPRESSION IN ELECTROMAGNETIC TRACKING SYSTEMS

(71) Applicant: Boston Scientific Scimed Inc., Maple Grove, MN (US)

(72) Inventors: Raju Viswanathan, Mountain View, CA (US); Jonathan Allen, Medford, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 266 days.

(21) Appl. No.: 15/838,952

(22) Filed: Dec. 12, 2017

(65) Prior Publication Data

US 2018/0168738 A1 Jun. 21, 2018

Related U.S. Application Data

(60) Provisional application No. 62/436,411, filed on Dec. 19, 2016.

(51) Int. Cl.
*A61B 34/20* (2016.01)
*A61M 25/01* (2006.01)
(Continued)

(52) U.S. Cl.
CPC .............. *A61B 34/20* (2016.02); *A61B 5/062* (2013.01); *A61M 25/0127* (2013.01); *A61B 5/7217* (2013.01); *A61B 2034/2051* (2016.02)

(58) Field of Classification Search
CPC ....... A61B 34/20; A61B 5/062; A61B 5/7217; A61B 2034/2051; A61M 25/0127
See application file for complete search history.

(56) References Cited

U.S. PATENT DOCUMENTS 5,377,678 A 1/1995 Dumoulin et al.
6,154,024 A 11/2000 Lewandowski et al.
(Continued)

FOREIGN PATENT DOCUMENTS

EP 0894473 A2 2/1999
WO 1996041119 A1 12/1996
WO 2006121740 A3 11/2006

OTHER PUBLICATIONS

Anonymous: "Fourier Series—Wikapedia", Nov. 26, 2016, Https:.. en.wikipedia.org/w/index.php?title=Fourier_series&oldid= 751622693 [retrieved on Mar. 20, 2018].
(Continued)

*Primary Examiner* — Bo Joseph Peng

(57) ABSTRACT

A method uses an electromagnetic tracking system, including a number of field transmitters and at least one receiver, to determine location information associated with a medical device. The method includes transmitting a set of electromagnetic signals, each signal having a frequency that is different than a frequency associated with each of the other signals, where each signal corresponds to a sum of sinusoidal functions, each of which includes an amplitude and a frequency. A field signal is received, and includes an undistorted field component and a distortion component. The amplitudes and frequencies of the sinusoidal functions are selected such that the distortion component includes a residual error arising from terms of at least a specified order in frequency. Field components corresponding to the field transmitters are extracted from the received signal, and the location information is determined based on the field components.

20 Claims, 3 Drawing Sheets

(51) Int. Cl.
*A61B 5/06* (2006.01)
*A61B 5/00* (2006.01)

(56) References Cited

U.S. PATENT DOCUMENTS

| | | |
|---|---|---|
| 6,172,499 B1 | 1/2001 | Ashe |
| 6,373,240 B1 | 4/2002 | Govari |
| 6,968,846 B2 | 11/2005 | Viswanathan |
| 8,942,780 B2 | 1/2015 | Scully et al. |
| 2008/0074307 A1* | 3/2008 | Boric-Lubecke .... A61B 5/0205 342/28 |

OTHER PUBLICATIONS

Bien, Tomasz; et al. "Electromagnetic Tracking System With Reduced Distortion Using Quadratic Excitation," Int J CARS (2014) 9:323-332.
International Search Report and Written Opinion issued in PCT/US2017/065763, dated Apr. 5, 2018, 16 pages.

* cited by examiner

DISTORTION SUPPRESSION IN ELECTROMAGNETIC TRACKING SYSTEMS

CROSS-REFERENCE TO RELATED APPLICATION

This application claims priority to Provisional Application No. 62/436,411, filed Dec. 19, 2016, which is herein incorporated by reference in its entirety.

TECHNICAL FIELD

Embodiments of the present disclosure relate to electromagnetic tracking systems. More specifically, embodiments of the disclosure relate to suppression of distortion due to conductors in an electromagnetic tracking environment.

BACKGROUND

Electromagnetic tracking systems are useful in medical device applications where the position and orientation of a medical device can often provide useful information in a minimally invasive or surgical medical procedure. Such systems often include a set of electromagnetic field generators (e.g., field transmitters) and one or more field sensors associated with a medical device that can measure signals from the set of transmitters. The measured signals are used with a computational algorithm to estimate the position and/or orientation of the medical device or a portion thereof (for example, the distal tip of a medical device).

Conductors (e.g., metals) in the environment of an electromagnetic tracking system can cause tracking errors, given that the transmitted field may be distorted in the presence of conductors. The transmitted fields can drive eddy currents in metals or other conductors in the environment around the transmitters, and these eddy currents in turn result in distortions of the transmitted fields. In procedures requiring a high degree of accuracy in position and/or orientation tracking, such field distortions can result in errors in position or orientation that negatively impact the medical procedure. It is therefore desirable to seek methods to suppress or mitigate such errors due to conductors in the environment of an electromagnetic tracking system.

While there have been previous attempts to address this problem, there is a need for a direct and simple-to-implement solution that does not place significant constraints on the hardware of a tracking system and does not result in significant additional computational demands. For example, conventional systems typically attempt to mitigate these types of errors by calibrating the system based on mathematical models of the distortion that are dependent upon properties of the particular conductors present in the environment. This approach is inflexible, as a change in the presence, position, orientation, etc., of conductors in the environment requires an evaluation of those conductors and an adjustment of the transmission parameters based on that evaluation, which also increases computational costs.

SUMMARY

Embodiments include methods and electromagnetic tracking systems for determining location information associated with a medical device. In embodiments, distortion due to conductors in the environment is suppressed by utilizing a parameter selection process designed to select frequencies and/or amplitudes, and to dynamically control the field transmitters, such that the distortion component of the resulting field received by the receiver includes a residual error arising from terms of at least a specified order in frequency. In this manner, embodiments facilitate distortion suppression without having to ascertain or otherwise consider properties of the specific conductors.

In an Example 1, a method for using an electromagnetic tracking system to determine location information associated with a medical device, the electromagnetic tracking system having a plurality of field transmitters and at least one receiver, the method comprising: transmitting, using a field transmitter of the plurality of field transmitters, a set of electromagnetic signals, each electromagnetic signal of the set of electromagnetic signals having a frequency that is different than a frequency associated with each of the other electromagnetic signals of the set of electromagnetic signals, wherein the set of electromagnetic signals corresponds to a sum of individual electromagnetic signals each in the form of sinusoidal functions, each of the sinusoidal functions comprising an amplitude and a frequency; receiving, from the at least one receiver, a received field signal corresponding to at least one transmitted set of electromagnetic signals, wherein the received field signal comprises an undistorted field component and a distortion component, wherein the amplitudes and frequencies of the sinusoidal functions comprising the transmitted set of electromagnetic signals are selected such that the distortion component of the received field signal comprises a residual error arising from terms of at least a specified order in frequency; extracting, from the received field signal, a plurality of field components corresponding to at least one of the plurality of field transmitters; and determining, based on the plurality of field components, location information associated with the medical device.

In an Example 2, the method of Example 1, the plurality of field transmitters comprising between two and sixteen field transmitters.

In an Example 3, the method of Example 2, the plurality of field transmitters comprising three field transmitters.

In an Example 4, the method of any of Examples 1-3, wherein the specified order in frequency comprises a third order.

In an Example 5, the method of any of Examples 1-4, the set of frequencies comprising a first frequency, a second frequency, and a third frequency, wherein: the first frequency is between at least approximately 800 Hz and 960 Hz; the second frequency is between at least approximately 1600 Hz and 1760 Hz; and the third frequency is between at least approximately 2400 Hz and 2560 Hz.

In an Example 6, the method of any of Examples 1-5, further comprising selecting the amplitudes and the frequencies of the sinusoidal functions.

In an Example 7, the method of Example 6, wherein selecting the amplitudes and the frequencies of the sinusoidal functions comprises solution of a system of equations.

In an Example 8, the method of Example 7, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

In an Example 9, the method of any of Examples 1-8, further comprising collecting performance information and adjusting, based on the performance information, at least one of the amplitudes of the sinusoidal functions.

In an Example 10, an electromagnetic tracking system, comprising: a plurality of field transmitters; at least one receiver; a field controller operatively coupled to the plurality of field transmitters, and configured to cause a field transmitter of the plurality of field transmitters to transmit a set of electromagnetic signals, each electromagnetic signal of the set of electromagnetic signals having a frequency that is different than a frequency associated with each of the other electromagnetic signals of the set of electromagnetic signals, wherein each electromagnetic signal is a sinusoid corresponding to a sum of sinusoidal functions, each of the sinusoidal functions comprising an amplitude and a frequency; and a signal processor configured to: receive, from the at least one receiver, a received field signal corresponding to at least one transmitted set of electromagnetic signals, wherein the received field signal comprises an undistorted field component and a distortion component; wherein the amplitudes and frequencies of the sinusoidal functions comprising the transmitted set of electromagnetic signals are selected such that the distortion component of the received field signal comprises a residual error arising from terms of at least a specified order in frequency; extract, from the received field signal, a plurality of field components corresponding to at least one of the plurality of field transmitters; and determine, based on the plurality of field components, location information associated with the medical device.

In an Example 11, the system of Example 10, the plurality of transmitters comprising between two and sixteen field transmitters.

In an Example 12, the system of either of Examples 10 or 11, wherein the specified order in frequency comprises a third order.

In an Example 13, the system of any of Examples 10-12, wherein the field controller is further configured to select the amplitudes and frequencies of the sinusoidal functions by solving a system of equations.

In an Example 14, the system of Example 13, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

In an Example 15, the system of any of Examples 1-14, wherein the field controller is further configured to collect performance information and adjust, based on the performance information, at least one of the amplitudes of the sinusoidal functions.

In an Example 16, a method for using an electromagnetic tracking system to determine location information associated with a medical device, the electromagnetic tracking system having a plurality of field transmitters and at least one receiver, the method comprising: transmitting, from each field transmitter of the plurality of field transmitters, a set of electromagnetic signals, each electromagnetic signal of the set of electromagnetic signals having a frequency that is different than a frequency associated with each of the other electromagnetic signals of the set of electromagnetic signals, wherein each electromagnetic signal is a sinusoidal function comprising an amplitude and a frequency; wherein no two frequencies in the transmitted sets of electromagnetic signals are identical; receiving, from the at least one receiver, a received field signal corresponding to each transmitted set of electromagnetic signals, wherein each received field signal comprises an undistorted field component and a distortion component; wherein the amplitudes and frequencies of the sinusoidal functions comprising each transmitted set of electromagnetic signals are selected such that the distortion component of each received field signal comprises a residual error arising from terms of at least a specified order in frequency; extracting, from each received field signal, a plurality of field components corresponding to at least one of the plurality of field transmitters; and determining, based on the plurality of field components, location information associated with the medical device.

In an Example 17, the method of Example 16, the plurality of field transmitters comprising between two and sixteen field transmitters.

In an Example 18, the method of Example 17, the plurality of field transmitters comprising three field transmitters.

In an Example 19, the method of Example 16, wherein the specified order in frequency comprises a third order.

In an Example 20, the method of Example 16, the set of frequencies comprising a first frequency, a second frequency, and a third frequency, wherein: the first frequency is between at least approximately 800 Hz and 960 Hz; the second frequency is between at least approximately 1600 Hz and 1760 Hz; and the third frequency is between at least approximately 2400 Hz and 2560 Hz.

In an Example 21, the method of Example 16, further comprising selecting the amplitudes and the frequencies of the sinusoidal functions.

In an Example 22, the method of Example 21, wherein selecting the amplitudes and the frequencies of the sinusoidal functions comprises solution of a system of equations.

In an Example 23, the method of Example 22, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

In an Example 24, the method of Example 16, further comprising collecting performance information and adjusting, based on the performance information, at least one of the amplitudes of the sinusoidal functions.

In an Example 25, an electromagnetic tracking system, comprising: a plurality of field transmitters; at least one receiver; a field controller operatively coupled to the plurality of field transmitters, and configured to cause a field transmitter of the plurality of field transmitters to transmit a set of electromagnetic signals, each electromagnetic signal of the set of electromagnetic signals having a frequency that is different than a frequency associated with each of the other electromagnetic signals of the set of electromagnetic signals, wherein each electromagnetic signal is a sinusoidal function comprising an amplitude and a frequency; and a signal processor configured to: receive, from the at least one receiver, a received field signal corresponding to each transmitted set of electromagnetic signals, wherein each received field signal comprises an undistorted field component and a distortion component; wherein the amplitudes and frequencies of the sinusoidal functions comprising each transmitted set of electromagnetic signals are selected such that the distortion component of each received field signal comprises a residual error arising from terms of at least a specified order in frequency; extract, from each received field signal, a plurality of field components corresponding to at least one of the plurality of field transmitters; and determine, based on the plurality of field components, location information associated with the medical device.

In an Example 26, the system of Example 25, the plurality of transmitters comprising between two and sixteen field transmitters.

In an Example 27, the system of Example 25, wherein the specified order in frequency comprises a third order.

In an Example 28, the system of Example 25, wherein the field controller is further configured to select the amplitudes and frequencies of the sinusoidal functions by determining amplitudes and frequencies that solve a system of equations.

In an Example 29, the system of Example 28, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

In an Example 30, the system of Example 25, wherein the field controller is further configured to collect performance information and adjust, based on the performance information, at least one of the amplitudes of the sinusoidal functions.

In an Example 31, the system of Example 25, the set of frequencies comprising a first frequency, a second frequency, and a third frequency, wherein: the first frequency is between at least approximately 800 Hz and 960 Hz; the second frequency is between at least approximately 1600 Hz and 1760 Hz; and the third frequency is between at least approximately 2400 Hz and 2560 Hz.

In an Example 32, a method for tracking a catheter using an electromagnetic tracking system having a plurality of field transmitters and at least one receiver, the method comprising: transmitting, using a first field transmitter of the plurality of field transmitters, a first set of electromagnetic signals, each electromagnetic signal of the first set of electromagnetic signals having a frequency that is different than a frequency associated with each of the other electromagnetic signals of the first set of electromagnetic signals, wherein each electromagnetic signal of the first set of electromagnetic signals is a sinusoid corresponding to a first sum of sinusoidal functions, each of the sinusoidal functions of the first sum comprising an amplitude and a frequency; transmitting, using a second field transmitter of the plurality of field transmitters, a second set of electromagnetic signals, each electromagnetic signal of the second set of electromagnetic signals having a frequency that is different than a frequency associated with each of the other electromagnetic signals of the second set of electromagnetic signals, wherein the second set of electromagnetic signals corresponds to a second sum of sinusoidal functions, each of the sinusoidal functions of the second sum comprising an amplitude and a frequency; receiving, from the at least one receiver, a received field signal corresponding to the first and second sets of electromagnetic signals, wherein the received field signal comprises an undistorted field component and a distortion component; wherein the amplitudes and frequencies of the sinusoidal functions comprising the transmitted sets of electromagnetic signals are selected such that the distortion component of the received field signal comprises a residual error arising from terms of at least a specified order in frequency; deconvolving the received electromagnetic signal to extract a first field component and a second field component, the first and second field components corresponding, respectively, to the first and second field transmitters; and determining, based on the first and second field components, at least one of a position of the at least one receiver and a location of the at least one receiver.

In an Example 33, the method of Example 32, wherein each electromagnetic signal of the second set of electromagnetic signals includes a frequency that is different than a frequency associated with each of the electromagnetic signals of the first set of electromagnetic signals.

In an Example 34, the method of Example 32, further comprising selecting the amplitudes and the frequencies of each of the sinusoidal functions of the first sum of sinusoidal functions by selecting amplitudes and frequencies that solve a system of equations.

In an Example 35, the method of Example 32, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
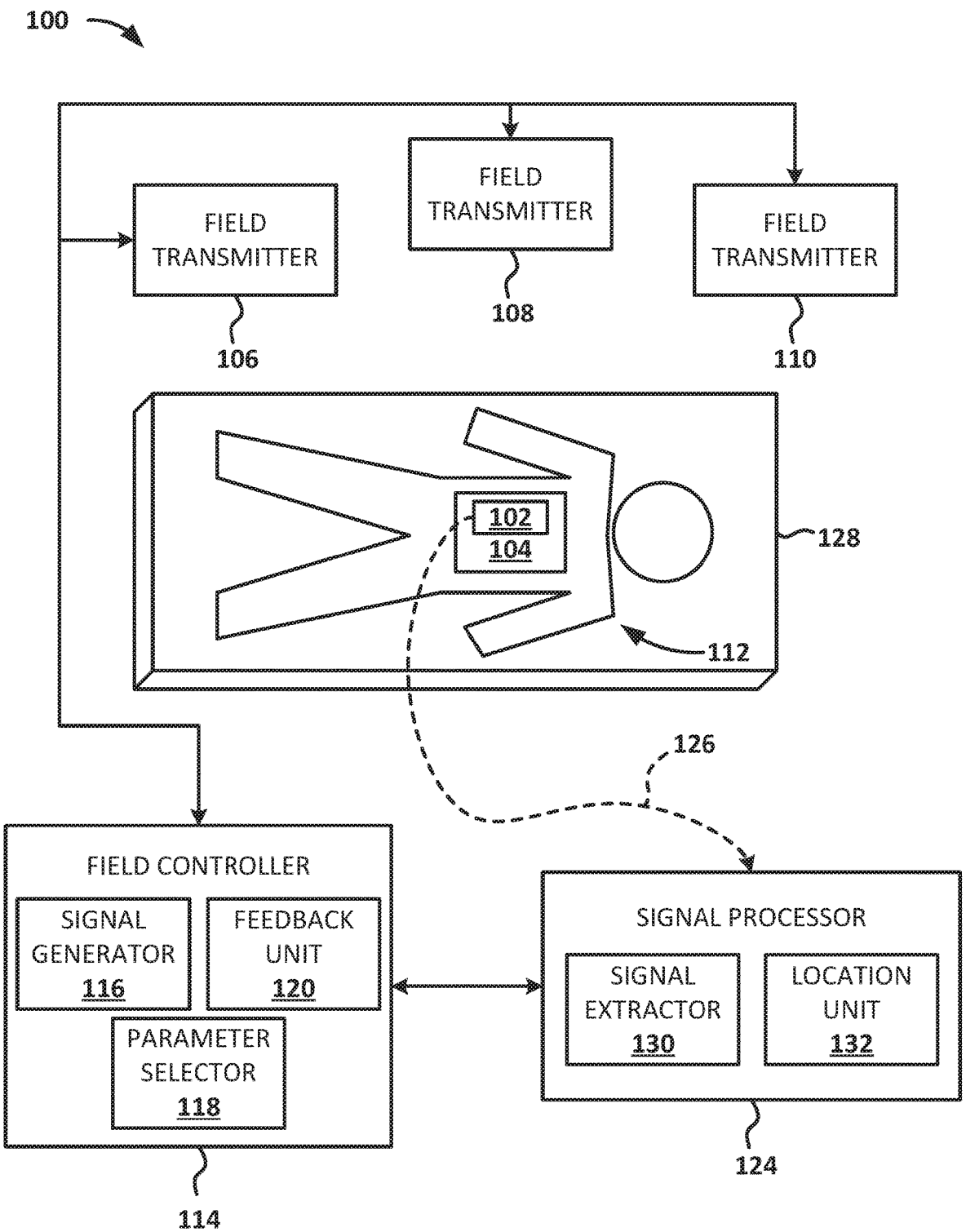
FIG. 1 is a schematic block diagram depicting an illustrative tracking system 100, in accordance with embodiments of the disclosed subject matter.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

FIG. 1 is a schematic block diagram depicting an illustrative electromagnetic tracking system 100, in accordance with embodiments of the disclosed subject matter. The tracking system 100 is configured to determine, based on information collected using a receiver 102 associated with a medical device 104, location information corresponding to the medical device 104. The information collected by the receiver 102 includes a received field signal corresponding to an electromagnetic field defined by a set of electromagnetic signals transmitted by field transmitters 106, 108, and 110. A field transmitter may include, for example, a spool, a coil, a trace, and/or the like. According to embodiments, two or more field transmitters 106, 108, and 110, are configured to transmit (e.g., radiate) sinusoidal electromagnetic signals, which produce a field within which a subject 112 is disposed. According to embodiments, the system 100 includes a field controller 114 configured to manage operation of the transmitters 106, 108, and 110.

As shown in FIG. 1, the field controller 114 includes a signal generator 116 configured to provide a driving current to each of the field transmitters 106, 108, and 110, thereby causing each field transmitter to transmit an electromagnetic signal based on the driven current. In embodiments, the signal generator 116 may be configured to provide sinusoidal driving currents to the field transmitters 106, 108, and 110. Various parameter values of the driving currents may be configured based on receiving the parameter values from a parameter selector 118.

The parameter selector 118 may be configured to select one or more parameter values corresponding to one or more of the electromagnetic signals to be transmitted by one or more of the field transmitters 106, 108, and 110. The selected parameter values may include values of parameters such as, for example, frequency, amplitude, wavelength, period, phase, power, and/or the like. In embodiments, the parameter selector 118 selects a parameter value by determining the value of the parameter that satisfies a specified relationship. For example, in embodiments, the parameter selector 118 may be configured to evaluate a system of equations to solve for an independent variable, where the solution includes a parameter value. In this manner, for example, each field transmitter may be configured to emit a sinusoidal signal having a weighted mixture of frequencies, with the respective amplitudes (e.g., weights) obtained from solving a set of equations designed to suppress error terms of increasing order in frequency. The set of transmission frequencies is unique for each transmitter coil, and the relative amplitudes for each coil may be monitored and controlled within a pre-defined range.

According to embodiments, the field controller 114 may include a feedback unit 120 that is configured to receive feedback information from the field transmitters 106, 108, and 110, the receiver 102, and/or a signal processor 124 to determine whether to adjust the transmitted electromagnetic signals. That is, for example, the field controller 114 may be configured to determine whether any number of different types of criteria are satisfied and, based on that determination, to cause the electromagnetic signals to be adjusted. The feedback unit 120 may be configured to cause an electromagnetic signal to be adjusted by providing a control signal to the signal generator 116 to cause the signal generator 116 to modify the driving current that it provides to the corresponding field transmitter, and/or by providing a control signal to the parameter selector 118 to cause the parameter selector 118 to modify one or more determined parameter values before the parameter selector 118 provides the one or more parameter to the signal generator 116. In this manner, embodiments may include a closed feedback loop that facilitates dynamically generating an electromagnetic field that satisfies any number of various types of criteria. For example, the feedback unit 120 may be configured to detect the occurrence of drift (e.g., due to heating of transmitter components), and may calculate an adjustment to adjust for the drift. In embodiments, for example, the feedback unit 120 may be configured to control the amplitudes of the signals (e.g., the weights associated with the frequencies, as explained below) so as to maintain a particular relationship between the amplitudes. For example, in embodiments, the feedback unit 120 is configured to maintain the relationship between the multiple transmitted amplitudes to be within 1% of the relationship between the selected amplitudes.

The receiver 102 (which may include one or more receivers) may be configured to produce an electrical response to the field—referred to herein as a received field signal. That is, for example, the receiver 102 may include a coil, a Hall probe, a Giant Magneto-Resistive (GMR) sensor, or other magnetic sensor, and the changing magnetic flux in the receiver 102 may induce voltages in the receiver 102. The received field signal may include multiple received field signals, each of which may be processed to extract field components corresponding to one or more transmitters. The received field signal is communicated to a signal processor 124, which is configured to analyze the received field signal to determine location information corresponding to the receiver 102 (and, thus, the medical device 104). Location information may include any type of information associated with a location and/or position of a medical device 104 such as, for example, location, relative location (e.g., location relative to another device and/or location), position, orientation, velocity, acceleration, and/or the like.

The medical device 104 may include, for example, a catheter (e.g., a mapping catheter, an ablation catheter, a diagnostic catheter, etc.), an implantable medical device (e.g., a control device, a monitoring device, a pacemaker, an implantable cardioverter defibrillator (ICD), a cardiac resynchronization therapy (CRT) device, a CRT-D device, etc.), and/or the like. For example, in embodiments, the medical device 104 may include a mapping catheter associated with an anatomical mapping system. The medical device 104 may include any other type of device configured to be at least temporarily disposed within a subject 112. The subject 112 may be a human, a dog, a pig, and/or any other animal having physiological parameters that can be recorded. For example, in embodiments, the subject 112 may be a human patient.

As shown in FIG. 1, the medical device 104 may be configured to be disposed within the body of a subject 112, and may be configured to be communicatively coupled to the signal processor 124 via a communication link 126. In embodiments, the communication link 126 may be, or include, a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 126 may be a persistent communication link, an intermittent communication link, an ad-hoc communication link, and/or the like. The communication link 126 may refer to direct communications between the medical device 104 and the signal processor 124, and/or indirect communications that travel between the medical device 104 and the signal processor 124 via at least one other device (e.g., a repeater, router, hub, and/or the like). The communication link 126 may facilitate uni-directional and/or bi-directional communication between the medical device 104 and the signal processor 124. Data and/or control signals may be transmitted between the medical device 104 and the signal processor 124 to coordinate the functions of the medical device 104 and/or the signal processor 124.

In operation, the time-varying electromagnetic field produced using the transmitters 106, 108, and 110 may be distorted by the presence of conductors within the environment. For example, as shown in FIG. 1, the subject 112 may be positioned on a conductive platform 128 (e.g., a metal bed), the room in which the subject 112 is disposed may include conductive medical equipment, structures, and/or the like. It will be understood by those having skill in the relevant arts that a time-varying electromagnetic field may produce eddy currents within a conductor, which may have distortive effects on the resulting electromagnetic field that is detected by the receiver 102.

Given a set of field transmitters each emitting an electromagnetic field (e.g., an electromagnetic signal), the field distortions due to conductors (e.g., metals) in the environment can be written as a power series expansion in powers of frequency. Embodiments of the subject matter disclosed herein include a technique that uses a specific mixture of frequencies in the transmitted signal so as to suppress successive terms involving powers of frequency in such an expansion, and that uses the resulting received signal as an estimate of the zero frequency signal. In this approach, an intent is to eliminate the first few or first several terms up to a certain order in a frequency expansion, leaving only the undistorted field and a set of higher order terms representing residual error. In embodiments, this is automatically accomplished by use of an appropriate mixture of transmitted signal parameters.

As mentioned above, induced currents are generated in a conductor in the presence of the time-varying magnetic field emitted by the transmitters. In the following, it is assumed, without loss of generality, that the receiver 102 is an inductive receiver. A similar analysis can be performed for the case of non-inductive sensors (for example, GMR sensors, etc.). If the transmitted field is given by a time-dependent function with a sinusoidal variation that generates a magnetic field B(t) at the receiver 102, it is not hard to see that the induced currents in the conductor 128 result in a magnetic field distortion at the receiver 102 that can be written as:

$$\Delta B \propto b_1 f'(t) + b_2 f''(t) + b_3 f'''(t) + \ldots \quad (1)$$

where the prime denotes a time derivative and $b_1$, $b_2$, etc. are (in general, complex-valued) coefficients that depend on the geometry of the conductor and on the relative separation vector between the receiver 102 and the conductor 128. For a given frequency of excitation, the coefficients $b_m$ generally depend on frequency. For example, for sinusoidal excitations, the derivatives become powers of frequency $\omega$, and the products $|b_m|\omega^m$ can be shown to be a (generally rapidly) decreasing series over the frequency range of interest. Correspondingly, the induced voltage or signal in the receiver 102 has a distortion contribution that can be written as:

$$\Delta s(t) \propto b_1 f'(t) + b_2 f''(t) + b_3 f'''(t) + \ldots \quad (2).$$

For excitation at a single sinusoidal frequency, $\omega$, $$f(t) = \sin \omega t,$$

the field distortion can be rewritten in the form:

$$\Delta B = c_1 \omega \cos(\omega t + \phi_1) - c_2 \omega^2 \sin(\omega t + \phi_2) - c_3 \omega^3 \cos(\omega t + \phi_3) + \ldots \quad (3)$$

where the (now real) coefficients $c_1$, $c_2$, $c_3$, etc. as well as the phases $\phi_1$, $\phi_2$, $\phi_3$, etc. are in general functions of frequency, $\omega$. These quantities can also be expanded as series expansions of powers of frequency. The net field measured by the sensor can be rewritten again (after expansion) in the form:

$$B = B_0 \sin \omega t + \Delta B = B_0 \sin \omega t + d_1 \omega \cos(\omega t + \psi_1) - d_2 \omega^2 \sin(\omega t + \psi_2) - d_3 \omega^3 \sin(\omega t + \psi_3) \quad (4)$$

where $B_0$ is the (frequency-independent) undistorted B-field, and the coefficients $d_i$ and phases $\psi_i$ in the expansion are now constants. The undistorted field $B_0$ is the component of the received field signal that is used by the signal processor 124 to determine location information corresponding to the medical device 104. As shown in FIG. 1, the signal processor 124 includes a signal extractor 130, which may be configured to extract, from the received field signal, signal components associated with each of the field transmitters 106, 108, and 110 (e.g., by deconvolving the received signal). Throughout this document, the term "deconvolve" and its derivatives (e.g., deconvolving, deconvolved, etc.) is used herein to refer to a process of "deconvolution," refers to an operation that reverses effects of convolution. In this context, "deconvolving" and its derivatives are interchangeable with the term "deconvolute" and its derivatives (e.g., deconvoluting, deconvoluted, etc.) to the extent that those terms also refer to a process of deconvolution. The signal processor 124 further includes a location unit 132 configured to determine, based on the extracted signal components, location information corresponding to the medical device 104. The location unit 132 may be configured to determine location information according to any location-determination technique that uses magnetic tracking.

To reduce the distortive effect of the conductor 128 on the received field signal, in embodiments, the parameter selector 118 may be configured to select a set of frequency values and frequency weights (e.g., amplitude terms associated with the frequency values) that satisfies a relationship (e.g., a system of equations). In embodiments, the parameter selector 118 may be configured to select values $a_1$, $a_2$, and $a_3$ as amplitudes for three frequencies $\omega_1$, $\omega_2$, and $\omega_3$, respectively, so that the transmitted signal (from a single transmitter coil) is proportional to:

$$T(t)=a_1 \sin \omega_1 t + a_2 \sin \omega_2 t + a_3 \sin \omega_3 t. \quad (5)$$

The distorted field equation (4) then becomes a sum of similar terms at each frequency.

The received signal can be deconvolved with each of the three frequencies, and the received field can be written as:

$$S = \frac{1}{(a_1+a_2+a_3)} \sum_{i=1}^{3} \langle s(t) \sin \omega_i t \rangle \quad (6)$$

where the brackets < > indicate a normalized time integral. When distortions are not present (no metal in the environment), equation (6) directly yields the undistorted field $B_0$.

In embodiments, the parameter selector 118 may be configured to select amplitude coefficients $a_1$, $a_2$, and $a_3$ such that $$a_1 \omega_1 + a_2 \omega_2 + a_3 \omega_3 = 0$$

$$a_1 \omega_1^2 + a_2 \omega_2^2 + a_3 \omega_3^2 = 0. \quad (7)$$

In this case, in the presence of metal in the environment, the distorted field may be represented as in equation (4) above, and equation (6) for the received field yields:

$$S = B_0 + \Sigma_i 0(\omega_i^3) \quad (8)$$

where the last term is a residual error arising from higher order terms in frequency. This residual error can be made smaller by transmission of more frequencies with suitable amplitudes, to suppress respective terms of higher powers in frequency. Thus, from equation (8), it is evident that the undistorted field, $B_0$ is recovered up to an error of cubic order in frequency, by selection of amplitudes of three frequencies such that equations (7) are satisfied. In embodiments, the parameter selector 118 may be configured to select as many frequencies as desired to suppress more and more error terms. The parameter selector 118 and feedback unit 120 can be integrated in embodiments, and may act as a control loop that serves to maintain the relative amplitudes of the transmitted mixture of frequencies. The control feedback loop may employ principles of control theory as well known and practiced in the art, such as Proportional-Integral-Derivative (PID) control, closed-loop transfer functions, and/or the like. In embodiments, the control feedback loop may employ one or more nonlinear control methods.

As a non-limiting example, assume transmission of three frequencies from each field transmitter. Without loss of generality, suppose the parameter selector 118 selects $a_1=1$. Then equations (7) become $$a_1 + a_2 \omega_2 + a_3 \omega_3 = 0$$

$$\omega_1^2 + a_2 \omega_2^2 + a_3 \omega_3^2 = 0. \quad (9)$$

In the signal reconstruction provided by equation (6), if the frequencies $\omega_1$, $\omega_2$, and $\omega_3$, are quite close to each other, the denominator ($a_1+a_2+a3$) can become quite small and noise in the received signal, s(t), can be amplified due to a small magnitude of this denominator. In order to mitigate this effect, the frequencies must be relatively spaced out. Thus, for example, the parameter selector 118 may select the frequencies $\omega_1=800$ Hz, $\omega_2=1600$ Hz, and $\omega_3=2400$ Hz, and, by solving the system of equations (9) above, the parameter selector may determine that $a_1=1$, $a_2=-1$, and $a_3=\frac{1}{3}$. Thus, a first field transmitter in this example may be configured to transmit a signal at 800 Hz, 1600 Hz, and 2400 Hz. Different field transmitters transmit different sets of frequencies, with each frequency being uniquely used. In embodiments, for each set of frequencies, the frequencies may be configured to be within two to three bandwidths of one another. In this example, and for purposes of non-limiting illustration only, the bandwidth of the system may be in the range of at least approximately 40 Hz. Using this bandwidth in the example discussed immediately above, a second transmitter may be configured to transmit a signal at 880 Hz, 1680 Hz, and 2480 Hz; and a third transmitter may be configured to transmit a signal at 960 Hz, 1760 Hz, and 2560 Hz. Thus, each transmitter may be configured to transmit a distinct set of frequencies, with no two frequencies (in the entire system) being identical. Furthermore, the frequencies may be separated by at least two system bandwidths (e.g., 2×40 Hz=80 Hz, in this example). The selected frequencies may be any frequency in the range that can be useful for electromagnetic tracking of an object such as a medical device, subject to the constraints of unique frequencies and sufficient separation as described above. In embodiments, for example, the frequencies may be greater than at least approximately 300 Hz and less than at least approximately 12,000 Hz.

The illustrative electromagnetic tracking system 100 shown in FIG. 1 is not intended to suggest any limitation as to the scope of use or functionality of embodiments of the present disclosure. Neither should the illustrative system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure. For example, the field controller 114 and signal processor 124 may be implemented on a common computing device, using a common software module, and/or the like. As another example, in embodiments, any one or more of the signal generator 116, the parameter selector 118, and the feedback unit 120 may be integrated into one or more program components. Similarly, the signal extractor and/or the location unit 132 may be integrated into one or more program components.

Figure 2:
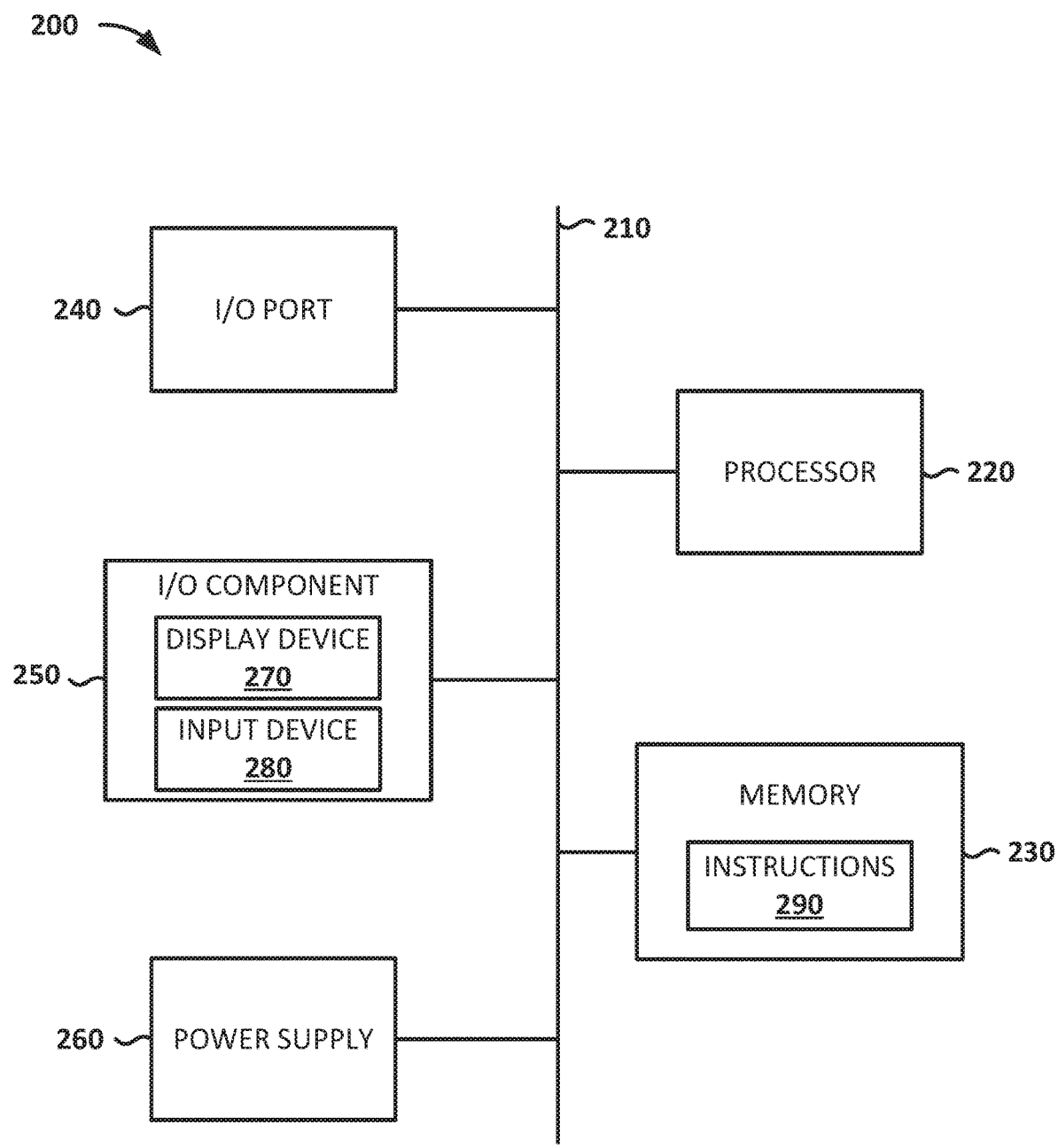
FIG. 2 is a block diagram depicting an illustrative computing device 200, in accordance with embodiments of the disclosed subject matter.

According to various embodiments of the disclosed subject matter, any number of the components depicted in FIG. 1 (e.g., the receiver 102, the medical device 104, the field controller 114, and/or the signal processor 124 may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 270 for causing the processor 220 to implement aspects of embodiments of system components discussed herein and/or to perform aspects of embodiments of methods and procedures discussed herein.

The computer-executable instructions 270 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
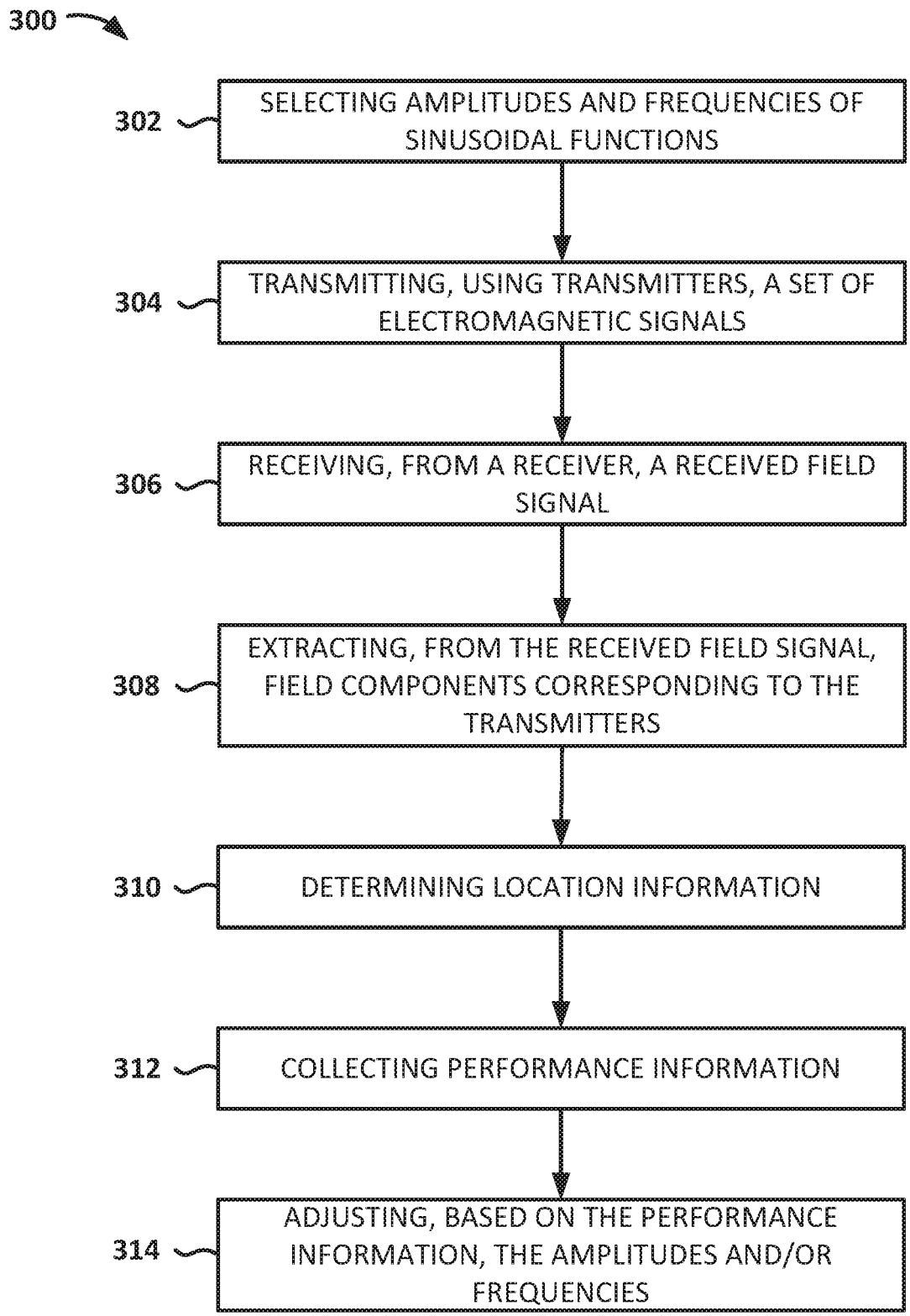
FIG. 3 is a flow diagram depicting an illustrative method for using an electromagnetic tracking system to determine location information associated with a medical device, in accordance with embodiments of the disclosed subject matter.

Embodiments of an electromagnetic tracking system have been described herein, in which each of a number of field transmitters transmits a number of electromagnetic signals, each signal having a different frequency, with the relative proportions of individual frequencies in the combination of frequencies being selected to reduce a distortion component of the field signal received by a receiver. FIG. 3 is a flow diagram depicting an illustrative method 300 for using an electromagnetic tracking system to determine location information associated with a medical device. Embodiments of the method 300 may be performed by one or more components of an electromagnetic tracking system such as, for example, the tracking system 100 depicted in FIG. 1. In embodiments, the electromagnetic tracking system may include two or more field transmitters and at least one receiver. For example, the system may include between two and sixteen field transmitters. In embodiments, the system may include at least three field transmitters, each of which transmits electromagnetic signals with at least three different frequencies.

As shown in FIG. 3, embodiments of the method 300 include selecting amplitudes and frequencies of sinusoidal functions for driving the field transmitters (block 302). As explained above, selecting the amplitudes and the frequencies of the sinusoidal functions may include determining amplitudes and frequencies of the sinusoidal functions that solve a system of equations. In embodiments, the system of equations may include a first equation and a second equation, the first equation having a sum of first-order product terms, each first-order product term including a product of one of the amplitudes and a corresponding frequency, and the second equation having a sum of second-order product terms, each second-order product term including a product of one of the amplitudes and a square of a corresponding frequency.

Sets of electromagnetic signals are transmitted using field transmitters (block 304). Each electromagnetic signal of a set of electromagnetic signals being transmitted by a field transmitter may include a frequency that is different than a frequency associated with each of the other electromagnetic signals of the set of electromagnetic signals. In embodiments, each set of electromagnetic signals is a combination of sinusoids corresponding to a sum of individual sinusoidal functions, where each of the individual sinusoidal functions includes an amplitude and a frequency. For example, embodiments may include transmitting, using a first field transmitter, a first set of electromagnetic signals, each electromagnetic signal of the first set of electromagnetic signals having a frequency that is different than a frequency associated with each of the other electromagnetic signals of the first set of electromagnetic signals, where each electromagnetic signal of the first set of electromagnetic signals is a sinusoid including an amplitude and a frequency, with the combined first set of electromagnetic signals corresponding to a first sum of these sinusoidal functions. Similarly, embodiments may include transmitting, using a second field transmitter, a second set of electromagnetic signals, each electromagnetic signal of the second set of electromagnetic signals having a frequency that is different than a frequency associated with each of the other electromagnetic signals of the second set of electromagnetic signals, where each electromagnetic signal of the second set of electromagnetic signals is a sinusoid including an amplitude and a frequency, with the combined second set of electromagnetic signals corresponding to a second sum of these sinusoidal functions. In embodiments, each electromagnetic signal of the second set of electromagnetic signals may include a frequency that is different than a frequency associated with each of the electromagnetic signals of the first set of electromagnetic signals.

As is further depicted in FIG. 3, in embodiments, a field signal is received (block 306) and field components corresponding to the transmitters are extracted from the received field signal (block 308). The received field signal corresponds to a field including (e.g., generated by) the set of electromagnetic signals. In embodiments, the received field signal includes an undistorted field component and a distortion component, where the amplitudes and frequencies of the sinusoidal functions are selected such that the distortion component includes a residual error arising from terms of at least a specified order in frequency. According to embodiments, the specified order in frequency may include any specified order such as, for example, the second order, the third order, the fourth order, and/or the like. According to an illustrative example embodiment, the set of frequencies may include a first frequency, a second frequency, and a third frequency, where the first frequency is between at least approximately 800 Hz and 960 Hz; the second frequency is between at least approximately 1600 Hz and 1760 Hz; and the third frequency is between at least approximately 2400 Hz and 2560 Hz. According to embodiments, extracting the field components may include deconvolving the received electromagnetic signal.

As is shown, embodiments of the method 300 further include determining location information (block 310). According to embodiments, the method 300 may further include collecting performance information (block 312) and adjusting, based on the performance information, the amplitudes and/or frequencies of the transmitted signals (block 314) such as, for example, to account for drift. In embodiments, the steps 302 to 314 of the location determination process are carried out continuously and repetitively over a succession of time steps that collectively define a larger time interval. In embodiments, the larger time interval may correspond to at least a portion of a medical procedure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for using an electromagnetic tracking system to determine location information associated with a medical device, the electromagnetic tracking system having a plurality of field transmitters and at least one receiver, the method comprising:
   transmitting, from each field transmitter of the plurality of field transmitters, a set of electromagnetic signals, each electromagnetic signal of the set of electromagnetic signals having a frequency that is different than a frequency associated with each of the other electromagnetic signals of the set of electromagnetic signals, wherein each electromagnetic signal is a sinusoidal function comprising an amplitude and a frequency;
   wherein no two frequencies in the transmitted sets of electromagnetic signals are identical;
   receiving, from the at least one receiver, a received field signal corresponding to each transmitted set of electromagnetic signals, wherein each received field signal comprises an undistorted field component and a distortion component;
   wherein the amplitudes and frequencies of the sinusoidal functions comprising each transmitted set of electromagnetic signals are selected such that the distortion component of each received field signal comprises a residual error arising from terms of at least a specified order in frequency;
   extracting, from each received field signal, a plurality of field components corresponding to at least one of the plurality of field transmitters; and
   determining, based on the plurality of field components, location information associated with the medical device.

2. The method of claim 1, the plurality of field transmitters comprising between two and sixteen field transmitters.

3. The method of claim 2, the plurality of field transmitters comprising three field transmitters.

4. The method of claim 1, wherein the specified order in frequency comprises a third order.

5. The method of claim 1, the set of frequencies comprising a first frequency, a second frequency, and a third frequency, wherein:
   the first frequency is between at least approximately 800 Hz and 960 Hz;
   the second frequency is between at least approximately 1600 Hz and 1760 Hz; and
   the third frequency is between at least approximately 2400 Hz and 2560 Hz.

6. The method of claim 1, further comprising selecting the amplitudes and the frequencies of the sinusoidal functions.

7. The method of claim 6, wherein selecting the amplitudes and the frequencies of the sinusoidal functions comprises solution of a system of equations.

8. The method of claim 7, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

9. The method of claim 1, further comprising collecting performance information and adjusting, based on the performance information, at least one of the amplitudes of the sinusoidal functions.

10. An electromagnetic tracking system, comprising:
   a plurality of field transmitters;
   at least one receiver;
   a field controller operatively coupled to the plurality of field transmitters, and configured to cause a field transmitter of the plurality of field transmitters to transmit a set of electromagnetic signals, each electromagnetic signal of the set of electromagnetic signals having a frequency that is different than a frequency associated with each of the other electromagnetic signals of the set of electromagnetic signals, wherein each electromagnetic signal is a sinusoidal function comprising an amplitude and a frequency; and
   a signal processor configured to:
      receive, from the at least one receiver, a received field signal corresponding to each transmitted set of electromagnetic signals, wherein each received field signal comprises an undistorted field component and a distortion component;
      wherein the amplitudes and frequencies of the sinusoidal functions comprising each transmitted set of electromagnetic signals are selected such that the distortion component of each received field signal comprises a residual error arising from terms of at least a specified order in frequency;
      extract, from each received field signal, a plurality of field components corresponding to at least one of the plurality of field transmitters; and
      determine, based on the plurality of field components, location information associated with the medical device.

11. The system of claim 10, the plurality of transmitters comprising between two and sixteen field transmitters.

12. The system of claim 10, wherein the specified order in frequency comprises a third order.

13. The system of claim 10, wherein the field controller is further configured to select the amplitudes and frequencies of the sinusoidal functions by determining amplitudes and frequencies that solve a system of equations.

14. The system of claim 13, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

15. The system of claim 10, wherein the field controller is further configured to collect performance information and adjust, based on the performance information, at least one of the amplitudes of the sinusoidal functions.

16. The system of claim 10, the set of frequencies comprising a first frequency, a second frequency, and a third frequency, wherein:
  the first frequency is between at least approximately 800 Hz and 960 Hz;
  the second frequency is between at least approximately 1600 Hz and 1760 Hz; and
  the third frequency is between at least approximately 2400 Hz and 2560 Hz.

17. A method for tracking a catheter using an electromagnetic tracking system having a plurality of field transmitters and at least one receiver, the method comprising:
  transmitting, using a first field transmitter of the plurality of field transmitters, a first set of electromagnetic signals, each electromagnetic signal of the first set of electromagnetic signals having a frequency that is different than a frequency associated with each of the other electromagnetic signals of the first set of electromagnetic signals, wherein each electromagnetic signal of the first set of electromagnetic signals is a sinusoid corresponding to a first sum of sinusoidal functions, each of the sinusoidal functions of the first sum comprising an amplitude and a frequency;
  transmitting, using a second field transmitter of the plurality of field transmitters, a second set of electromagnetic signals, each electromagnetic signal of the second set of electromagnetic signals having a frequency that is different than a frequency associated with each of the other electromagnetic signals of the second set of electromagnetic signals, wherein the second set of electromagnetic signals corresponds to a second sum of sinusoidal functions, each of the sinusoidal functions of the second sum comprising an amplitude and a frequency;
  receiving, from the at least one receiver, a received field signal corresponding to the first and second sets of electromagnetic signals, wherein the received field signal comprises an undistorted field component and a distortion component;
  wherein the amplitudes and frequencies of the sinusoidal functions comprising the transmitted sets of electromagnetic signals are selected such that the distortion component of the received field signal comprises a residual error arising from terms of at least a specified order in frequency;
  deconvolving the received electromagnetic signal to extract a first field component and a second field component, the first and second field components corresponding, respectively, to the first and second field transmitters; and
  determining, based on the first and second field components, at least one of a position of the at least one receiver and a location of the at least one receiver.

18. The method of claim 17, wherein each electromagnetic signal of the second set of electromagnetic signals includes a frequency that is different than a frequency associated with each of the electromagnetic signals of the first set of electromagnetic signals.

19. The method of claim 17, further comprising selecting the amplitudes and the frequencies of each of the sinusoidal functions of the first sum of sinusoidal functions by selecting amplitudes and frequencies that solve a system of equations.

20. The method of claim 17, wherein the system of equations includes a first equation and a second equation, the first equation comprising a sum of first-order product terms, each first-order product term comprising a product of one of the amplitudes and a corresponding frequency, and the second equation comprising a sum of second-order product terms, each second-order product term comprising a product of one of the amplitudes and a square of a corresponding frequency.

* * * * *